United States Patent
Geier et al.

(10) Patent No.: US 6,758,082 B2
(45) Date of Patent: Jul. 6, 2004

(54) SEALING SYSTEM FOR A GAS SENSOR AND A METHOD FOR MANUFACTURING THE SEALING SYSTEM

(75) Inventors: Heinz Geier, Leonberg (DE); Helmut Weyl, Schwieberdingen (DE); Siegfried Nees, Neckarwestheim (DE); Bernhard Wild, Markgroeningen (DE); Thomas Egner, Kornwestheim (DE); Peter Dettling, Waiblingen (DE)

(73) Assignee: Robert Bosch GmbH, Stuttgart (DE)

(*) Notice: Subject to any disclaimer, the term of this patent is extended or adjusted under 35 U.S.C. 154(b) by 109 days.

(21) Appl. No.: 10/143,048

(22) Filed: May 10, 2002

(65) Prior Publication Data

US 2003/0015020 A1 Jan. 23, 2003

(30) Foreign Application Priority Data

May 12, 2001 (DE) .......................... 101 23 168

(51) Int. Cl.⁷ ................... G01N 7/00; G01N 33/497; G01N 27/26; F16J 15/08
(52) U.S. Cl. ............... 73/31.05; 73/23.31; 204/424; 277/650
(58) Field of Search ................ 73/23.31, 23.32, 73/31.05; 204/424–429; 277/650, 957

(56) References Cited

U.S. PATENT DOCUMENTS

| | | | | |
|---|---|---|---|---|
| 4,040,930 A | * | 8/1977 | Dillon | 204/429 |
| 4,225,842 A | * | 9/1980 | Schlesselman et al. | 73/23.31 |
| 4,229,275 A | * | 10/1980 | Habdas et al. | 204/426 |
| 5,308,469 A | * | 5/1994 | Aldinger et al. | 204/426 |
| 5,725,218 A | * | 3/1998 | Maiya et al. | 277/650 |
| 5,755,941 A | * | 5/1998 | Weyl | 204/424 |
| 5,846,391 A | * | 12/1998 | Friese et al. | 204/424 |
| 6,124,224 A | * | 9/2000 | Sridharan et al. | 501/15 |
| 2001/0045120 A1 | * | 11/2001 | Friese et al. | 73/23.31 |

FOREIGN PATENT DOCUMENTS

| | | |
|---|---|---|
| DE | 195 32 090 | 3/1997 |
| DE | 19545590 A1 * | 6/1997 |
| DE | 196 15 866 | 10/1997 |
| DE | 197 07 456 | 8/1998 |
| DE | 198 52 674 | 5/2000 |
| EP | 0 704 698 | 4/1996 |
| EP | 0 706 046 | 4/1996 |

* cited by examiner

*Primary Examiner*—Michael Cygan
(74) *Attorney, Agent, or Firm*—Kenyon & Kenyon

(57) ABSTRACT

A gas sensor includes a sensor element for determining at least one physical quantity of a gas, e.g., for determining the concentration of a gas component in an exhaust gas of an internal combustion engine or the temperature of the exhaust gas. The sensor element is fixed in position by the sealing system in a housing of the gas sensor. The sealing system includes at least one sealing element, which includes a mixture of a ceramic material and a glass. The hemisphere temperature of the glass is above 750° Celsius.

30 Claims, 2 Drawing Sheets

SEALING SYSTEM FOR A GAS SENSOR AND A METHOD FOR MANUFACTURING THE SEALING SYSTEM

FIELD OF THE INVENTION

The present invention relates to a sealing system for a gas sensor and a method for manufacturing the sealing system.

BACKGROUND INFORMATION

A sealing system of this type is described in German Published Patent Application No. 198 52 674. This sealing system uses a sealing element made of a mixture of steatite and a glass having a low melting point. The low-melting-point glass includes lead, zinc, bismuth or alkaline-earth metals in the form of oxides, borates, phosphates, or silicates. The sealing system is pressed between two solid-sintered molded ceramic parts and it separates a measuring-gas-side segment of a sensor element, secured in a housing of the gas sensor, from a connection-side segment of the sensor element, the connection-side segment protruding into a reference gas chamber, which is acted upon by a reference gas. To manufacture the sealing system, a compressed sealing ring is inserted into the longitudinal bore hole and is pressed between the two molded ceramic parts. Subsequently, the sealing ring is subjected to a thermal treatment at a temperature between 500 and 700° Celsius. As a result of the thermal treatment, the glass powder in the steatite matrix is melted and partially diffuses into the pores of the steatite matrix.

At temperatures in the range of 500° Celsius and above, the insulation effect of the sealing system falls off considerably, so that the electrical resistance between the sensor element and housing, given the above-mentioned composition, is reduced to a value of less than 5 MΩ at a temperature of 500° Celsius. Therefore, between the sensor element and the housing, electrical currents may flow, which impair the functioning of the sensor element. In addition, the sealing system is not suitable for temperatures above 700° Celsius, because it includes a low-melting-point glass.

SUMMARY

The gas sensor according to the present invention may provide the advantage that it has a high electrical resistance between the sensor element and the housing, and it includes a sealing system including a sealing element that is gas-tight even at temperatures above 700° Celsius and that is impermeable to fluids, e.g., to fuels. For this purpose, the sealing element includes a mixture of ceramic material and glass, the glass having a hemisphere temperature of over 750° Celsius. The hemisphere temperature of a glass is determined by slowly heating a cylindrical figure having a diameter of 3 mm and a height of 3 mm. The hemisphere temperature is the temperature at which the body is deformed by the heating such that the height of the body corresponds exactly to one half of the diameter of the figure, i.e., 1.5 mm.

The method according to the present invention may provide the advantage that the manufacturing of the seal may be integrated in the mass production of gas sensors in a cost-effective manner.

The composition of the glass-forming materials may be selected so that the electrical resistance between the sensor element and the housing, at a temperature of 500° Celsius, is greater than 20 MΩ. For this purpose, glass-forming materials may be used which have a high resistance in a composite along with the ceramic material. In contrast, glass-forming materials having a lower resistance in a composite are only used in small quantities. These requirements may be met by a glass that includes a high proportion of barium, strontium, boron, zinc, and/or silicon, e.g., in the form of oxides. In contrast, the glass includes small proportions of iron, copper, lithium, sodium, potassium, magnesium, and/or calcium, also, e.g., in the form of oxides. The proportions of these components altogether are under 8 percent by weight and/or, with regard to individual components, under 5 percent by weight, in each case with regard to the glass. The proportions of these components altogether may be under 5 percent by weight and/or, with respect to the individual components, under 3 percent by weight.

The ceramic material may include steatite, boron nitride, forsterite, aluminum oxide, magnesium spinel, zirconium oxide, or zirconium oxide stabilized using calcium oxide, magnesium oxide, or yttrium oxide, or a mixture of the latter.

A temperature-resistant as well as gas-tight and gasoline-tight seal may be achieved if the sealing element includes a proportion of ceramic material of 45 to 90 percent by volume, e.g., 60 to 80 percent by volume, and a proportion of glass of 10 to 55 percent by volume, e.g., 20 to 40 percent by volume. To avoid mechanical stresses, the composition of the sealing element may be selected so that the thermal expansion coefficient of the glass is between $7 \cdot 10^{-6}$ K$^{-1}$ and $10 \cdot 10^{-6}$ K$^{-1}$, and the thermal expansion coefficient of the ceramic material is between $7 \cdot 10^{-6}$ K$^{-1}$ and $12 \cdot 10^{-6}$ K$^{-1}$.

In an example embodiment, the sealing system is configured in a so-called sandwich arrangement and includes a first, second, and third sealing element, the second sealing element being arranged between the first and the third sealing element. At least one of the sealing elements includes the mixture of the ceramic material and the glass. As further materials for the sealing elements, steatite, boron nitride, or a mixture of steatite and boron nitride may be provided. A sealing system may include a sealing element including steatite and/or boron nitride arranged between two glass-ceramic sealing elements, or a glass-ceramic sealing element arranged between two sealing elements including steatite and/or boron nitride, or a sealing element including steatite and/or boron nitride arranged between a glass-ceramic sealing element and a steatite sealing element. In the sealing systems described, the sealing action is strengthened even more by the combination of different materials.

If the sealing element is prefabricated before it is inserted into the housing of the gas sensor, by pressing the mixture of the ceramic powder and a glass-forming powder in a pressing method forming a sealing ring, and by simultaneously and/or subsequently subjecting it to a temperature of 300 to 600° Celsius, then the sealing ring will be strengthened to the point that it has the necessary stability when it is installed in the housing. Because the glass, in this context, is only heated to a temperature significantly below the hemisphere temperature, a plastic deformation of the prefabricated sealing ring is possible under the influence of a pressure force, after installation in the housing. In this context, it is possible, using deformation, to adjust the prefabricated sealing ring to a longitudinal bore hole of the housing and to the sensor element. Subsequently, the pre-assembled assembly is subjected to a thermal treatment at a temperature of 750 to 1000° Celsius, e.g., 800 to 900° Celsius, as a result of which the sealing element is formed. In this thermal treatment, the glass-forming powder in the mixture is melted and diffuses at least partially into the pores of the ceramic powder. The thermal treatment may also be performed before and/or during the application of the pressing force.

As a result of the thermal treatment of the mixture of the ceramic powder and the glass-forming powder, it is possible that in addition to the purely crystalline ceramic phases and the purely amorphous glass phases, glass ceramic phases are also formed, which arise due to the crystallization, e.g., of the glass-forming powder. The glass included in the sealing element should be understood as a material that exists in the amorphous glass phase and/or in the crystalline glass ceramic phase that arises under certain manufacturing conditions.

Example embodiments of the present invention are illustrated in the drawings and are described in greater detail below.

DETAILED DESCRIPTION

Figure 1:
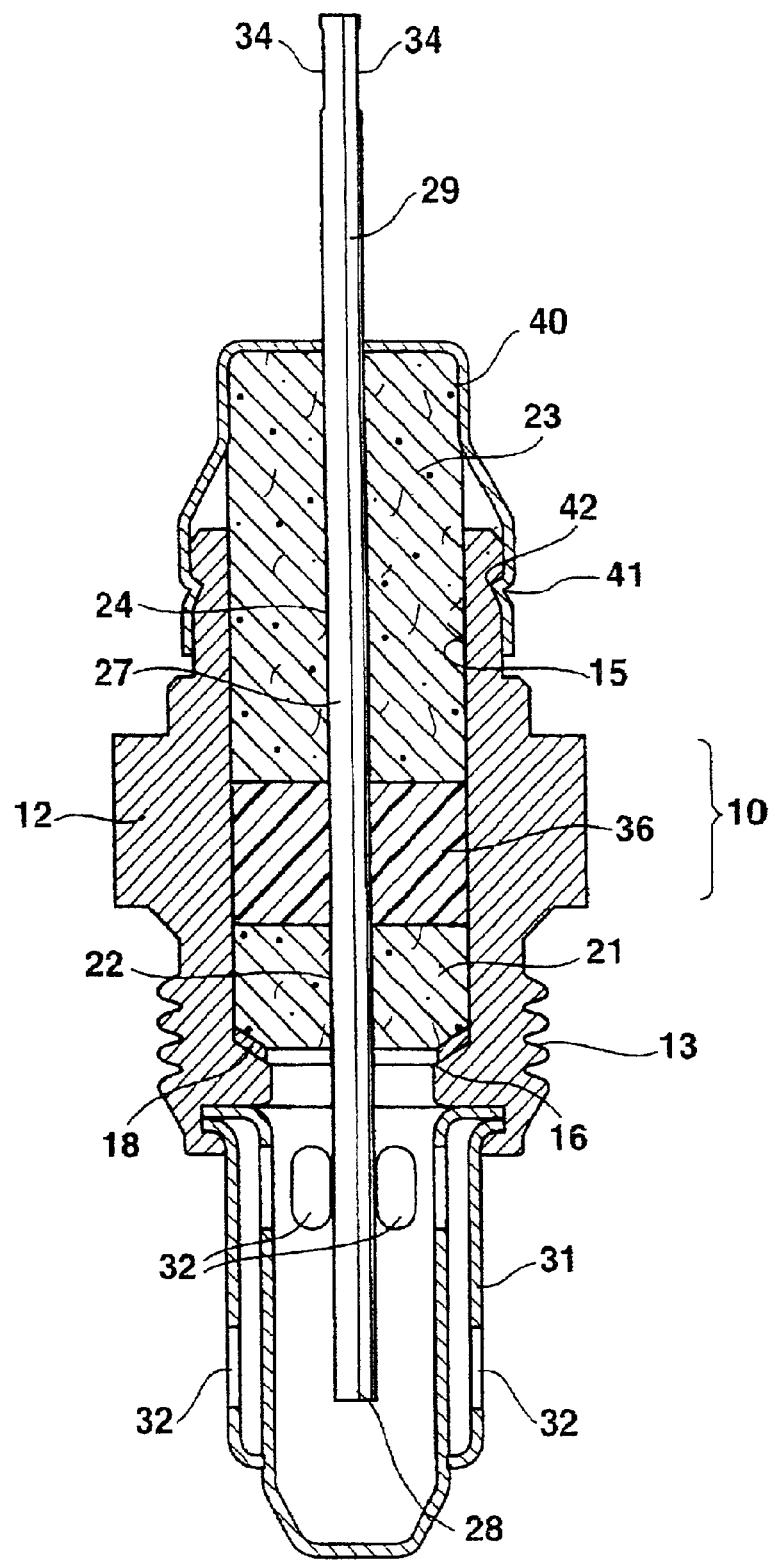
FIG. 1, as a first example embodiment of the present invention, is a cross-sectional view of one part of a gas sensor according to the present invention including a sealing system.

FIG. 1, as a first example embodiment, illustrates one part of a gas sensor, for example, of an electrochemical sensor for determining the oxygen concentration in an exhaust gas of an internal combustion engine or for determining the temperature of the exhaust gas of an internal combustion engine, including a sealing system 10, which is inserted into a metallic housing 12 and which fixes a plate-shaped sensor element 27 in position. Housing 12 includes a longitudinal bore hole 15 having a shoulder-like annular surface 16. Located on shoulder-like annular surface 16 is, for example, a metallic sealing ring 18, on which a measuring-gas-side molded ceramic part 21 rests. Measuring-gas-side molded ceramic part 21, extending in the direction of longitudinal bore hole 15, includes a straight-through measuring-gas-side opening 22. Housing 12 also includes a thread 13 as a fixing arrangement for installation in an undepicted exhaust gas pipe.

Arranged at a distance from measuring-gas-side molded ceramic part 21, in longitudinal bore hole 15, is also a connection-side molded ceramic part 23. Connection-side molded ceramic part 23, in the direction of longitudinal bore hole 15, also includes a centrally arranged and straight-through connection-side opening 24. Measuring-gas-side opening 22 of measuring-gas-side molded ceramic part 21 and connection-side opening 24 of connection-side molded ceramic part 23 extend in alignment with each other.

Sensor element 27, which includes a measuring-gas-side segment 28 and a connection-side segment 29, is arranged in openings 22, 24. Measuring-gas-side segment 28 of sensor element 27 protrudes out of housing 12 and is surrounded by a protective tube 31, which is secured on housing 12. Protective tube 31 includes intake and outlet openings 32 for the gas to be measured. On connection-side segment 29, sensor element includes connection contacts 34, which also protrude from housing 12. Connection contacts 34 are contacted by a plug-in contact furnished with a connecting cable. Connection-side segment 29 protruding from housing 12 is surrounded by an undepicted protective sleeve, which protects connection-side segment 29 from environmental influences and forms a reference gas chamber in its interior.

Located between measuring-gas-side molded ceramic part 21 and connection-side molded ceramic part 23 is a sealing system 10, which is pressed between two molded ceramic parts 21, 23 and which includes a sealing element 36. Even in the installed state, sealing arrangement 10 remains under a pressure force. The pressure force necessary for this purpose is applied by a metal sleeve 40, which presses on connection-side molded ceramic part 23. In this context, metal sleeve 40, in, for example, a uniformly distributed fashion, includes a plurality of claws 41, pointing to the inside, which engage with notches 42 formed in housing 12. However, it is possible to weld metal sleeve 40 to housing 12, or to exert the pressure force using a spring element.

Sealing element 36 is composed of a mixture of a ceramic material and a glass, the proportion of ceramic material may be 69 percent by volume and the proportion of glass may be 31 percent by volume. The ceramic material is made of steatite. The glass includes 41 percent by weight BaO, 23 percent by weight ZnO, 19 percent by weight $B_2O_3$, 7 percent by weight $SiO_2$, 6 percent by weight $Al_2O_3$, 2 percent by weight a mixture of MgO and CaO, 1.5 percent by weight a mixture of $Fe_2O_3$ and CuO, as well as 0.5 percent by weight a mixture of $Li_2O$, $Na_2O$, and $K_2O$, in each case with respect to the percentage of glass.

For manufacturing sealing element 36, a sealing ring, which is made of the aforementioned mixture of a ceramic powder and a fine glass powder, is shaped by a pressing process. Subsequently, the sealing ring is heated to a temperature of 300 to 600° Celsius, e.g., 450° Celsius, as a result of which the sealing ring achieves a greater stability, so that the installation of the sealing ring in the housing is made easier. After the insertion of the sealing ring into longitudinal bore hole 15 onto measuring-gas-side molded ceramic part 21 and after the placement of connection-side molded ceramic part 23 onto the sealing ring, a pressure force is applied via metal sleeve 40 for pressing the sealing ring. The plasticity of the sealing ring is adjusted by heating to 450° Celsius, so that the sealing ring is deformed by the pressure force.

After that, the sealing ring is subjected to a thermal treatment at approximately 800° Celsius, as a result of which sealing element 36 is formed. As a result of the thermal treatment, the glass powder in the steatite matrix is melted and partially diffuses into the pores of the same. As a result, the permeability to gaseous and fluid hydrocarbons is significantly reduced. It is also possible to perform the thermal treatment during the compression of the sealing ring.

Figure 2:
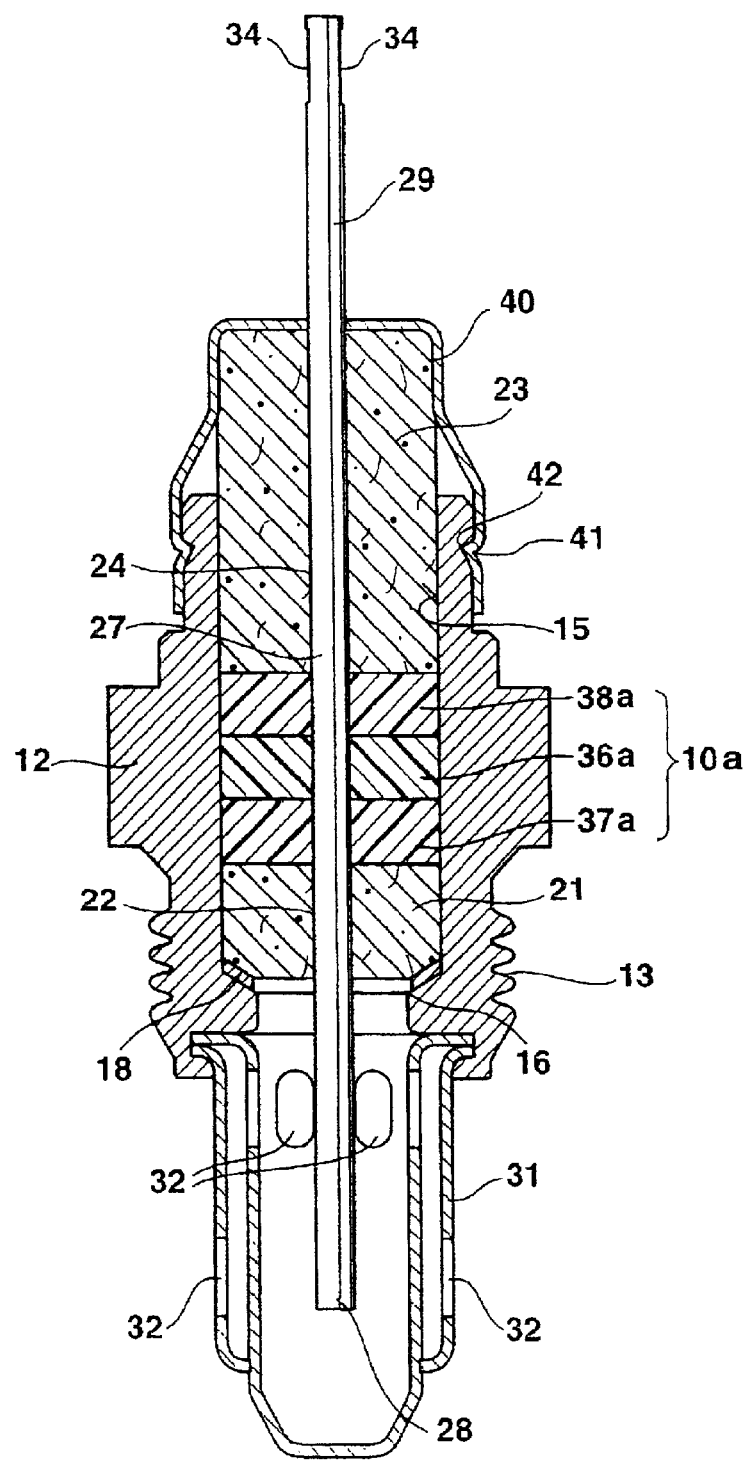
FIG. 2, as a second example embodiment of the present invention, is a cross-sectional view of one part of a gas sensor according to the present invention including a sealing system.

A second example embodiment for a gas sensor is illustrated in FIG. 2, the same elements being furnished with the same reference numerals. The gas sensor includes a sealing system 10a including a first sealing element 36a, a second sealing element 37a, and a third sealing element 38a. First sealing element 36a is provided on the side of sealing system 10a that is facing measuring-gas-side segment 28 of sensor element 27. Arranged between first and third sealing elements 36a, 38a is second sealing element 37a.

In a first model of the second example embodiment, the composition of first and third sealing elements 36a, 38a corresponds to the composition of sealing element 36 according to the first example embodiment. Second sealing element 37a is composed of steatite, boron nitride, or a mixture of steatite and boron nitride.

In a second model of the second example embodiment, second sealing element 37a has the composition of sealing element 36 in accordance with the first example embodiment. First and third sealing elements 36a, 38a are composed of steatite, boron nitride, or a mixture of steatite and boron nitride.

A third model of the second example embodiment includes first sealing element 36a having the composition of sealing element 36 in accordance with the first example embodiment. Second sealing element 37a includes, as an component, boron nitride or steatite or a mixture of boron nitride and steatite, third sealing element 38a including steatite. In the third model, all possible combinations of positions of first, second, and third sealing elements 36a, 37a, 38a are possible. First sealing element 36a may be provided on the side of sealing system 10a that is facing away from measuring-gas-side segment 28 of sensor element 27, and third sealing element 38a may be provided on the side of sealing system 10a that is facing measuring-gas-side segment 28 of sensor element 27.

The use of sealing system 10, 10a, according to the present invention, is not limited to the sealing of planar sensor elements in metallic housings. It is possible to use a sealing element of this type, or a sealing system of this type, also for sealing so-called finger probes. In this application case, the execution of the pre-pressed sealing rings may be adjusted to the geometry of the longitudinal bore hole and to that of the contact surface of the housing and of the finger-shaped sensor element.

What is claimed is:

1. A gas sensor, comprising:
   a housing;
   a sensor element configured to determine at least one physical quantity of a gas; and
   a sealing system configured to fix the sensor element in position in the housing, the sealing system including at least one sealing element which includes a mixture of a ceramic material and a glass;
   wherein a hemisphere temperature of the glass is greater than 750° Celsius; and
   wherein the sealing system, at a temperature of 500° Celsius, has an electrical resistance between the sensor element and the housing of more than 20 MΩ.

2. The gas sensor according to claim 1, wherein the physical quantity includes at least one of a concentration of a gas component in an exhaust gas of an internal combustion engine and a temperature of the exhaust gas.

3. The gas sensor according to claim 1, wherein the hemisphere temperature of the glass is between 800 and 1,000° Celsius.

4. The gas sensor according to claim 1, wherein the glass includes as a significant component one of barium, an oxide of barium, strontium, an oxide of strontium, boron, an oxide of boron, zinc, an oxide of zinc, silicon, an oxide of silicon and a mixture thereof.

5. The gas sensor according to claim 1, wherein the glass includes a proportion of at least one of iron, an oxide of iron, copper, an oxide of copper, lithium, an oxide of lithium, sodium, an oxide of sodium, potassium, an oxide of potassium, magnesium, an oxide of magnesium, calcium, and an oxide of calcium in each case of less than 5 percent by weight.

6. The gas sensor according to claim 5, wherein the proportion of the at least one of iron, the oxide of iron, copper, the oxide of copper, lithium, the oxide of lithium, sodium, the oxide of sodium, potassium, the oxide of potassium, magnesium, the oxide of magnesium, calcium, and the oxide of calcium in each case of less than 3 percent by weight.

7. The gas sensor according to claim 1, wherein the glass includes a proportion of at least one of iron, an oxide of iron, copper, an oxide of copper, lithium, an oxide of lithium, sodium, an oxide of sodium, potassium, an oxide of potassium, magnesium, an oxide of magnesium, calcium, and an oxide of calcium altogether of under 8 percent by weight.

8. The gas sensor according to claim 7, wherein the proportion of the at least one of iron, the oxide of iron, copper, the oxide of copper, lithium, the oxide of lithium, sodium, the oxide of sodium, potassium, the oxide of potassium, magnesium, the oxide of magnesium, calcium, and the oxide of calcium altogether of under 5 percent by weight.

9. The gas sensor according to claim 1, wherein the glass includes a proportion of aluminum oxide of less than 25 percent by weight.

10. The gas sensor according to claim 1, wherein the sealing element includes a proportion of ceramic material of 45 to 90 percent by volume and a proportion of glass of 10 to 55 percent by volume.

11. The gas sensor according to claim 1, wherein the sealing element includes a proportion of ceramic material of 60 to 80 percent by volume and a proportion of glass of 20 to 40 percent by volume.

12. The gas sensor according to claim 1, wherein a thermal expansion coefficient of the glass is between $7$–$10^{-6}$ $K^{-1}$ and $10$–$10^{-6}$ $K^{-1}$.

13. The gas sensor according to claim 1, wherein a thermal expansion coefficient of the ceramic material is between $7$–$10^{-6}$ $K^{-1}$ and $12$–$10^{-6}$ $K^{-1}$.

14. The gas sensor according to claim 1, wherein the ceramic material includes at least one of steatite, boron nitride, forsterite, $Al_2O_3$, magnesium spinel, $ZrO_2$, $ZrO_2$ stabilized with CaO, MgO, $Y_2O_3$, and a mixture thereof.

15. The gas sensor according to claim 1, wherein the sensor element is fixed in position in a longitudinal bore hole of the housing by the sealing system, the sealing system separating a measuring-gas-side segment of the sensor element from a connection-side segment of the sensor element in at least one of a gas-tight manner and fluid-tight manner.

16. The gas sensor according to claim 1, wherein the sealing system is arranged in a longitudinal bore hole of the housing between a measuring-gas-side ceramic part and a connection-side molded ceramic part.

17. The gas sensor according to claim 1, further comprising a pressure element one of directly and indirectly joined to the housing configured to press on at least one of a measuring-gas-side ceramic part and connection-side molded ceramic part.

18. The gas sensor according to claim 1, wherein the sealing system includes a first sealing element, a second sealing element, and a third sealing element, the second sealing element arranged between the first sealing element and the third sealing element.

19. The gas sensor according to claim 18, wherein the first sealing element is arranged on a side facing a measuring-gas-side segment of the sensor element.

20. The gas sensor according to claim 18, wherein the first sealing element includes the mixture of ceramic material and glass, the third sealing element has the same composition as the first sealing element, and the second sealing element includes one of steatite, boron nitride, and a mixture of steatite and boron nitride.

21. The gas sensor according to claim 18, wherein the second sealing element includes the mixture of ceramic material and glass, and the first sealing element and the third sealing element include one of steatite, boron nitride, and a mixture of steatite and boron nitride.

22. The gas sensor according to claim 18, wherein the first sealing element, the second sealing element, and the third sealing element include at least one of a mixture of ceramic material and glass, steatite, boron nitride, and a mixture of steatite and boron nitride.

23. The gas sensor according to claim 22, wherein the first sealing element includes the mixture of ceramic material and glass, the second sealing element includes steatite, and the third sealing element includes one of boron nitride, steatite, and a mixture of boron nitride and steatite.

24. The gas sensor according to claim 22, wherein the first sealing element includes one of boron nitride, steatite, and a mixture of boron nitride and steatite, the second sealing element includes steatite, and the third sealing element includes the mixture of ceramic material and glass.

25. A method for manufacturing a sealing system including a housing, a sensor element configured to determine at least one physical quantity of a gas, and a sealing system configured to fix the sensor element in position in the housing, the sealing system including at least one sealing element which includes a mixture of a ceramic material and a glass, a hemisphere temperature of the glass greater than 750° Celsius, comprising the steps of:

inserting into the housing a prefabricated sealing ring including a mixture of a ceramic powder and a glass-forming powder;

plastically deforming the prefabricated sealing ring under a pressure force in a longitudinal bore hole of the housing; and subjecting the prefabricated sealing ring to a thermal treatment, in which the glass is melted;

wherein the sealing system, at a temperature of 500° Celsius, has an electrical resistance between the sensor element and the housing of more than 20 MΩ.

26. The method according to claim 25, wherein a temperature of the thermal treatment is between 750 and 1000° Celsius.

27. The method according to 26, wherein the temperature of the thermal treatment is between 800 and 900° Celsius.

28. The method according to claim 25, wherein the thermal treatment step is performed at least one of before, during, and after an application of the pressure force.

29. The method according to claim 25, further comprising the step of prefabricating the sealing ring by at least one of pressing and shaping the mixture of the ceramic powder and the glass-forming powder in a pressure method and subjecting it to a temperature of 300 to 600° Celsius.

30. The method according to claim 25, further comprising the step of prefabricating the sealing ring by at least one of pressing and shaping the mixture of the ceramic powder and the glass-forming powder in a pressure method and subjecting it to a temperature of 350 to 500° Celsius.

* * * * *